United States Patent
Candelon et al.

(10) Patent No.: US 9,011,676 B2
(45) Date of Patent: Apr. 21, 2015

(54) PROCESS FOR ELIMINATION OF MERCURY CONTAINED IN A HYDROCARBON FEED WITH HYDROGEN RECYCLING

(71) Applicant: AXENS, Rueil Malmaison Cedex (FR)

(72) Inventors: Jean Christophe Candelon, Nanterre (FR); Annick Pucci, Croissy sur Seine (FR); Clotilde Jubin, Boulogne Billancourt (FR)

(73) Assignee: AXENS, Rueil Malmaison Cedex (FR)

( * ) Notice: Subject to any disclaimer, the term of this patent is extended or adjusted under 35 U.S.C. 154(b) by 0 days.

(21) Appl. No.: 13/776,774

(22) Filed: Feb. 26, 2013

(65) Prior Publication Data
US 2013/0225897 A1 Aug. 29, 2013

(30) Foreign Application Priority Data
Feb. 27, 2012 (FR) ...................................... 12 00563

(51) Int. Cl.
*C07C 7/148* (2006.01)
*C10G 25/03* (2006.01)
*C10G 25/00* (2006.01)
*C10G 45/08* (2006.01)
*C10G 67/06* (2006.01)

(52) U.S. Cl.
CPC .............. *C07C 7/148* (2013.01); *C10G 25/003* (2013.01); *C10G 45/08* (2013.01); *C10G 67/06* (2013.01); *C10G 2300/205* (2013.01); *C10G 2300/4081* (2013.01)

(58) Field of Classification Search
None
See application file for complete search history.

(56) References Cited

U.S. PATENT DOCUMENTS

| 4,911,825 A | 3/1990 | Roussel et al. |
| 5,062,948 A | 11/1991 | Kawazoe et al. |
| 5,384,040 A | 1/1995 | Mank et al. |
| 5,401,392 A | 3/1995 | Courty et al. |
| 2002/0139721 A1 | 10/2002 | Didillon et al. |
| 2010/0025184 A1 | 2/2010 | Shibuya et al. |

FOREIGN PATENT DOCUMENTS

| FR | 2628338 A1 | 9/1989 |
| FR | 2803597 A1 | 7/2001 |

OTHER PUBLICATIONS

Search Report for FR 1200563 (Sep. 17, 2012).

*Primary Examiner* — Tam M Nguyen
(74) *Attorney, Agent, or Firm* — Millen, White, Zelano & Branigan, P.C.

(57) ABSTRACT

Elimination of mercury contained in a hydrocarbon feed by:
a) feed 1 is mixed with a hydrogen stream 14 and a gaseous fraction 13 originating from c),
b) mixture 1a contacted with a catalyst to convert mercury compounds to elemental mercury producing an effluent containing elemental mercury 6,
c) effluent containing elemental mercury is cooled to between 20° C. and 80° C., then, at 1.5 MPa and 3.5 MPa and between 20° C. and 80° C., separation 10 of said effluent containing the elemental mercury into a gaseous fraction 11 and a liquid fraction 15, at least a part of said gaseous fraction 11 being recycled to step a),
d) fractionation 20 of liquid fraction 15 to produce a gaseous phase 42 and a liquid phase 21, and
e) contacting at least a part of gaseous phase 42 with a mercury collection material 43.

12 Claims, 1 Drawing Sheet

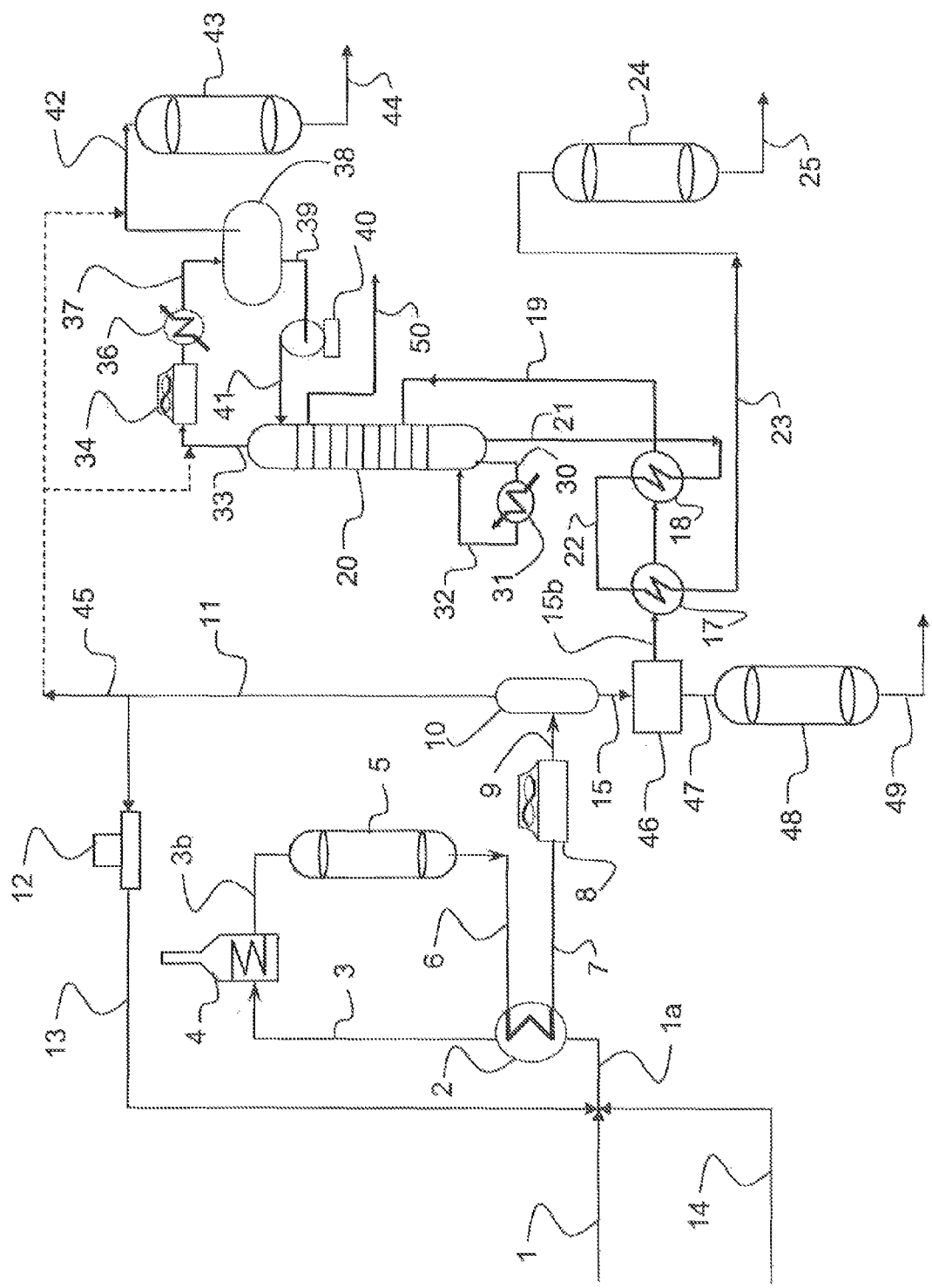

PROCESS FOR ELIMINATION OF MERCURY CONTAINED IN A HYDROCARBON FEED WITH HYDROGEN RECYCLING

The present invention relates to the field of the elimination of mercury contained in a liquid hydrocarbon feed.

The liquid condensates contained in a natural gas and certain crude oils can contain many metallic compounds, in particular mercury and arsenic, as traces and often in all types of forms: particulate or colloidal, ionic complexes or organometallics. These metallic compounds are very often poisonous to the catalysts used during refining and the conversion of these petroleum products to commercial products. Mercury is particularly toxic to the activity of precious metals, it is strongly corrosive to aluminium parts, joints and welds and, moreover, it is harmful to the environment and human health.

It is therefore necessary to scrub the feeds intended to be sent to the processes of refining and conversion of the natural gas or crude oil condensates in order to prevent mercury entrainment. The scrubbing of the feed upstream of the treatment processes makes it possible to protect all of the refinery installations.

U.S. Pat. No. 5,384,040 describes a process for the elimination of the mercury contained in a liquid hydrocarbon feed by successively carrying out the following steps:
- a step of hydrotreatment of the feed in the presence of a catalyst and hydrogen,
- a step of fractionation of the hydrotreated effluent into two or more than two fractions,
- a step of treatment of the lightest fraction by contact with a mercury collection material.

The present invention proposes to improve the process described by U.S. Pat. No. 5,384,040 by carrying out a gas/liquid separation step after the hydrotreatment step and by recycling a fraction of the separated gas upstream of the hydrotreatment step.

The invention generally describes a process for elimination of mercury contained in a liquid hydrocarbon feed comprising mercury compounds, in which the following steps are carried out:
- a) the feed is mixed with a hydrogen stream and a gaseous fraction originating from step c),
- b) the mixture obtained in step a) is brought into contact with a catalyst in order to convert the mercury compounds to elemental mercury so as to produce an effluent containing elemental mercury,
- c) said effluent containing elemental mercury is cooled to a temperature comprised between 20° C. and 80° C., then, at a pressure comprised between 1.5 MPa and 3.5 MPa and at a temperature comprised between 20° C. and 80° C., a separation of said effluent containing the elemental mercury into a gaseous fraction and a liquid fraction is carried out, at least a part of said gaseous fraction being recycled to step a), then
- d) a fractionation of said liquid fraction is carried out in order to produce a gaseous phase and a liquid phase,
- e) at least a part of the gaseous phase produced in step d) is brought into contact with a mercury collection material.

According to the invention, step b) can be carried out at a temperature comprised between 270° C. and 360° C. and at a pressure comprised between 1.5 MPa and 7 MPa.

The fractionation of step d) can be carried out at a pressure comprised between 0.5 MPa and 2.0 MPa such that said liquid phase can comprise at least 95% by weight of the throughput of the liquid hydrocarbon feed.

A portion of said gaseous fraction obtained in step c) can be drawn off and discharged from the process and said portion of said gaseous fraction can be mixed with the gaseous phase produced in step d).

The catalyst can comprise at least one element chosen from nickel and cobalt, said element being arranged on a support chosen from the group formed by alumina, silica-aluminas, silica, zeolites, activated carbon, clays and aluminous cements.

The collection material can comprise at least one of the following elements: copper oxide, lead oxide, copper sulphide, lead sulphide, sulphur on alumina, activated carbon, doped molecular sieves.

Step d) can be carried out in a distillation column, the gaseous phase being obtained directly at the head of the distillation column. Alternatively, step d) can be carried out in a distillation column, the gaseous stream produced at the head of the distillation column being partially condensed by cooling so as to produce said gaseous phase and a condensate which can be recycled at the head of the column as reflux.

Step e) can be carried out at a temperature below 150° C. and with a VVH comprised between 1 and 50 $h^{-1}$.

Before step d), the water contained in the liquid fraction can be extracted. The extracted water can be brought into contact with a mercury collection material.

The liquid phase obtained in step d) can be brought into contact with a mercury collection material.

The liquid phase produced in step d) can be divided and separated into a first liquid part and a second liquid part, the first liquid part comprising lighter compounds than the compounds of the second liquid part, and the first liquid part can be brought into contact with a mercury collection material. The first liquid part comprising the light compounds can have a final distillation point below 100° C.

BRIEF DESCRIPTION OF THE DRAWINGS

FIG. 1 represents a schematic of one embodiment of the invention.

Other characteristics and advantages of the invention will be better understood and will become clearly apparent on reading the description made below with reference to FIG. 1.

In FIG. 1, the hydrocarbon feed enters through the pipe 1. The liquid feed consists of hydrocarbon compounds, for example originating from liquid condensates contained in a natural gas, crude oils, or cuts extracted from liquid condensates or crude oils. For example the feed is composed of condensates of gas, a gasoline cut, for example a straight-run gasoline, a kerosene cut or a gas oil cut. The hydrocarbon feed contains mercury compounds, for example in amounts comprised between 0.001 and 5 milligrams of mercury per kilogram of feed. The mercury compounds can be mercury in particulate or colloidal, ionic complex or organometallic form. The hydrocarbon feed can also contain sulphur up to an amount comprised between 0 and 4% by weight of total sulphur. The feed flowing in the pipe 1 can be at a pressure comprised between 0.1 and 7 MPa, preferably between 1 and 5 MPa.

The feed 1 is mixed with hydrogen entering through the pipe 14 and with the recycled stream entering through the pipe 13. The mixture obtained is sent through the pipe 1a into the heat exchanger 2 then introduced into the combustion furnace 4 in order to be brought to a high temperature, for example comprised between 270° C. and 360° C., preferably between 280° C. and 350° C., more preferably between 290° C. and 345° C.

The hot fluid originating from the furnace 4 through the pipe 3b is introduced into the hydrotreatment reactor 5 in order to convert the mercury compounds to elemental mercury. In the reactor 5, the organo-sulphur compounds, in particular the mercaptans, are converted to hydrocarbon compounds and to hydrogen sulphide ($H_2S$).

The reactor 5 is operated under the following conditions:
temperature comprised between 270° C. and 360° C., preferably between 280° C. and 350° C., more preferably between 290° C. and 345° C.
pressure comprised between 1.5 and 7 MPa, preferably between 2 and 4 MPa.

The ratio of the hydrogen throughput in liters to the feed throughput in liters, introduced into the reactor 5, is comprised between 30 and 500 l/l, and preferably between 60 and 200 l/l.

The reactor 5 contains a solid catalyst that promotes hydrogenolysis of organo-mercury and arsenic compounds, as well as conventional hydrotreatment reactions which allow the sulphur and nitrogen of the feeds to be converted to $H_2S$ and $NH_3$, ammonia which is capable of recombining to form ammonium salts. Thus, the mercury compounds contained in the feed are converted to metallic mercury, while the arsenic compounds are collected on the catalyst after hydrogenolysis. The catalyst can comprise at least nickel or cobalt, preferably a catalyst based on nickel and molybdenum or a catalyst based on cobalt and molybdenum is used.

The support for the catalyst of reactor 5 can be chosen from the group formed by alumina, silica-aluminas, silica, zeolites, activated carbon, clays and aluminous cements. Preferably, an alumina support is used. Preferably, the support has a large surface area, a sufficient pore volume and an adequate average diameter of the pores. For example, the BET surface area of the support is greater than 50 $m^2/g$ and preferably comprised between 100 and 350 $m^2/g$. The support can have a pore volume, measured by nitrogen desorption, of at least 0.5 $cm^3/g$ and preferably comprised between 0.6 and 1.2 $cm^3/g$, and an average diameter of the pores at least equal to $70 \times 10^{-10}$ m and preferably greater than $80 \times 10^{-10}$ m.

The effluent originating from the reactor 5 through the pipe 6 is cooled by heat exchange in the heat exchanger 2, with mixing of the hydrocarbon feed with the hydrogen flowing in the pipe 1a. The cooled effluent is then introduced into the cooling means 8 (for example a heat exchanger or an air cooler) in order to be cooled by an ambient fluid, for example water or air. The effluent can be cooled down to a temperature comprised between 20° C. and 80° C., preferably between 30° C. and 60° C. The effluent originating from 8 is introduced, through the pipe 9, into the gas-liquid separator 10, for example a separator flask. Preferably, the pressure in the flask 10 is comprised between 1.5 and 3.5 MPa. The temperature in the flask 10 can be comprised between 20° C. and 80° C., preferably between 30° C. and 60° C.

The gas discharged from 10 through the pipe 11 mainly comprises excess hydrogen which has not reacted, $H_2S$ formed in the reactor 5 and mercury essentially in metallic form and the gaseous state. The gas 11 is recompressed in order to be brought to the pressure of the reactor in the compressor 12. The gas is then recycled through the pipe 13 in order to be mixed with the hydrocarbon feed entering through the pipe 1. Thus, the added portion of hydrogen through the pipe 14 can be limited to a throughput which makes it possible to compensate for the quantity of hydrogen consumed in the reactor 5. Operation is preferably with zero purge, i.e. all of the gas discharged through the pipe 11 is recycled in order to be mixed with the feed entering through the pipe 1. Nevertheless, a fraction of the gas flowing in the pipe 11 can be extracted and purged through the pipe 45 in order to prevent the accumulation of impurities in the recycling loop, in particular non-condensables such as nitrogen or CO or $CO_2$, which can be contained in the added hydrogen. In this case, the mercury-rich purge material can advantageously be mixed with the gaseous phase 33 or the gaseous stream 42 produced in the downstream fractionation step, in order to eliminate the mercury therefrom on the collection material 43 described below.

The metallic mercury which concentrates in the gaseous phase passes through the reactor 5 without disturbing its operation and finally exits in the liquid stream discharged from the flask 10. The liquid stream separated in the flask 10 exits through the pipe 15.

According to a first embodiment, the liquid stream flowing in the pipe 15 is introduced, through the pipe 15b, directly into the heat exchangers 17 and 18 in order to be heated. In this embodiment the elements numbered 46, 47, 48 and 49 are absent.

According to a second embodiment, an aqueous phase is injected into the stream flowing in the pipe 7 upstream of the cooling means 8 in order to dissolve the ammonium salts likely to form. The liquid stream flowing in the pipe 15 is introduced into the separator 46 in order to separate a liquid phase rich in water and a liquid phase rich in hydrocarbons. For example, the separator uses one of the following techniques: decanting, centrifugation, filtration, by absorption by a solvent, by adsorption on a collection material. The phase rich in hydrocarbons is discharged from the separator 46 through the pipe 15b in order to be introduced into the heat exchangers 17 and 18 in order to be heated. The phase rich in water is discharged from the separator 46 through the pipe 47.

According to the two embodiments, the hot liquid originating from the exchanger 18 is introduced, through the pipe 19, into the distillation column 20, commonly called stabilization column, in order to produce at least one gaseous phase and at least one liquid phase. The bottom of the column 20 is equipped with a reboiler 31. A liquid fraction is removed from the bottom of the column 20 through the pipe 30, heated by the reboiler 31, then re-introduced into the column 20 through the pipe 32. The column 20 is operated under pressure, for example comprised between 0.5 and 2.0 MPa. The column 20 makes it possible to separate a gaseous phase discharged through the pipe 33 at the head of the column and a liquid phase discharged at the bottom of the column through the pipe 21. The fractionation in the column 20 makes it possible to recover the gaseous phase 33 containing the hydrogen dissolved at the separator 10 and the non-condensables (methane, ethane, propane) which are introduced with the added hydrogen, the $H_2S$ and the metallic mercury. Typically, almost all of the feed 1 that has been hydrotreated, i.e. freed of the sulphur and nitrogen that it contained, is recovered at the bottom of column 20 at a temperature of the order of 150 to 250° C., the column being operated at a pressure comprised between 0.5 and 2.0 MPa in the case where the feed 1 is a straight-run gasoline. For example, the stream of liquid phase discharged from the column 20 through the pipe 21 comprises at least 95% by weight, preferably at least 98% by weight, or even at least 99% by weight, of the throughput of the feed entering through the pipe 1.

Optionally an intermediate liquid phase can be extracted from the column 20 through the pipe 50. In the case where the feed 1 is a straight-run gasoline, the liquid fraction 50 is composed of liquid petroleum gas, commonly called LPG.

The gaseous phase 33 is cooled in the heat exchangers 34 and 36 in order to be partially condensed, then introduced into the separator flask 38 through the pipe 37. The liquid part recovered at the bottom of the flask 38 is discharged through the pipe 39, pumped by the pump 40 then introduced at the head of the column 20 through the pipe 41 as reflux.

The gaseous stream discharged from the flask 38 through the pipe 42 comprises hydrogen, light hydrocarbons, in particular methane and ethane, as well as $H_2S$ and metallic mercury in the gaseous state. If the feed 1 is a straight-run gasoline, the gaseous stream 42 is mainly composed of hydrogen with light hydrocarbons from methane to butane, as well as mercury in the gaseous state and $H_2S$. In fact, according to the invention the act of carrying out a separation in the separator 10 under pressure, combined with recycling the gas 11 under pressure upstream of the reactor 5 makes it possible for almost all of the mercury in metallic form to be found in the gaseous phase 33 or in the gaseous stream 42 while maximizing the recovery of gasoline at the bottom of the column 20. This results from the fact that, after the separation in the flask 10, the gaseous fraction containing hydrogen and mercury in large quantities is recycled to the hydrotreatment reactor 5 preferably operated at a high temperature, consequently downstream during the fractionation in the column 20, the majority, or even all, of the mercury is concentrated in the gaseous phase 33. In the hydrotreatment step in the reactor 5, the majority of the mercaptans and other sulphur compounds are eliminated, hence the presence, in gas phase, of elemental mercury, or in other words of metallic mercury, in vapour phase, and of $H_2S$, with less than 0.5 ppm mercaptans. This makes it possible to avoid the formation of mercury compounds having a boiling point close to that of hydrocarbon compounds constituting a gasoline cut. These compounds are generally formed from mercaptans and mercury compounds because of the great affinity of mercury with mercaptans. The process according to the invention therefore makes it possible, under the temperature and pressure conditions used in the separator 20, to keep almost all, or even all, of the mercury recovered from the liquid fraction discharged at the bottom of the device 10, in the gaseous stream 42. Thus, according to the invention a single operation for collecting the mercury by treating only the gaseous stream 42 or the gaseous phase 33 can be carried out.

According to the invention, the gaseous stream discharged from 38 through the pipe 42 is brought into contact with the mercury collection material 43. The gaseous stream discharged from 43 through the pipe 44 is depleted, or even completely freed, of mercury. Alternatively, the gaseous phase 33 is treated directly by bringing this gaseous phase 33 into contact with a mercury collection material (this alternative is not shown in FIG. 1, in this case the collection material 43 treating the gaseous stream 42 is not used). This alternative has the advantage of returning a reflux 41 which is depleted of mercury to the head of column 20.

The mercury collection materials used in the process of the invention can be all those known to a person skilled in the art for collecting elemental mercury in gaseous or liquid phase. For example, a collection material composed of copper or lead oxide or copper or lead sulphide or sulphur on alumina, or else sulphur-containing or promoted activated carbon or optionally sulphur-containing mixed oxides of copper and zinc or iron can be used. In their regenerative version, these materials can be doped molecular sieves, preferably doped by means of at least one precious metal, more preferably doped with silver. One or more identical or different collection materials can be used for the same cut or different cuts and can optionally be distributed over several reactors in series or in parallel. Ion-exchange resins can also be envisaged for removing the mercury in aqueous phase.

Depending on the quantities of mercury contained in the feed, the ratio by volume of the catalyst of reactor 5 to the collection material 43 can vary between 15:1 and 2:1.

In order to ensure a good mercury collection efficiency, the temperature at which the collection in the collection material 43 is carried out, is below 150° C., preferably also below 100° C. and more preferably below 60° C. The space velocities calculated in relation to the collection material VVH (volume of feed per volume of material per hour) can be from 1 to 50 $h^{-1}$, and more particularly from 1 to 30 $h^{-1}$.

The maximum permissible amount of elemental mercury is a predetermined value which can be fixed by the process operator, in order to take into account corrosion effects and the quality of the products. Moreover, the maximum permissible amount of mercury can be fixed by national legislation, for example within the framework of environmental or health protection.

The liquid fraction discharged at the bottom of the column through the pipe 21 can be used to heat the stream 15b in the heat exchangers 18 and 17. The liquid fraction 23 can be upcycled directly without treatment to eliminate the mercury. If the feed 1 is a straight-run gasoline, the liquid fraction 23 is composed of a cut called hydrotreated "naphtha" which can be sent to a catalytic reforming unit.

In this case, to protect the reforming catalysts, the liquid fraction 23 can be brought into contact with the mercury collection material 24. The fraction discharged from 24 through the pipe 25 is depleted, or even completely freed, of mercury. If the feed 1 is an at least partially de-hexanized straight-run gasoline, the liquid fraction 24 is composed of a cut called "hydrotreated naphtha" which can be sent to a catalytic reforming unit.

Alternatively, if a wide-range gasoline is being treated, the liquid fraction 23 can be fractionated in a column (not shown in FIG. 1). In this case, the elements numbered 24 and 25 in FIG. 1 are not used, but a fractionation is used so as to obtain a light gasoline fraction which can be sent to an isomerization unit, and a heavy gasoline fraction which can be sent to a so-called catalytic reforming unit. The light fraction can have a final distillation point below 100° C. In this case, according to the invention, only the light gasoline fraction is brought into contact with a mercury collection material, but an elimination of mercury from the heavy gasoline fraction is not carried out. In fact, only the treatment of the light gasoline fraction is useful, because it concentrates the metallic mercury.

With reference to FIG. 1, optionally, the phase rich in water 47 discharged from the separator 46 is brought into contact with the mercury collection material 48 in order to eliminate the traces of dissolved mercury. The stream depleted of mercury is discharged from 48 through the pipe 49.

The different mercury collection materials used in the process, in particular the collection materials numbered 24 and 48 can have the same characteristics and be used under the same conditions as those described with reference to the mercury collection material 43.

In some of the most favourable cases of implementing the process according to the invention, the elimination of mercury in order to comply with the standards is carried out by only using the collection material 43 to eliminate the mercury from the gaseous part 42. In this case, a collection operation is not used on the aqueous phase 47, or on the liquid fraction 23.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 12/00.563, filed Feb. 27, 2012 are incorporated by reference herein.

The examples presented below allow the operation of the process according to the invention to be illustrated and compared with the prior art.

EXAMPLE 1

According to the Invention

This example is carried out according to the variant described with reference to FIG. 1 in which the separator 46, the collection materials 24 and 48 and the lines 47 and 49 are not used, but the mercury collection material 43 is used. In this example the ppm and ppb are expressed by weight.

100 tonnes/h of a feed 1 constituted by gasoline originating from the atmospheric fractionation of a gas condensate contaminated with mercury is treated. This C5-160° C. gasoline has a density of 0.72 kg/m$^3$ and contains 200 ppm by weight sulphur, 5 ppm by weight nitrogen and 190 ppb by weight mercury.

This feed 1 is mixed with 260 kg/h hydrogen at 78% purity entering through the pipe 14, before being brought to a temperature of at least 280° C., then introduced into the hydrotreatment reactor 5 where the reactions of desulphuration, denitrogenation and hydrogenolysis of the mercury compounds into elemental mercury take place simultaneously.

The reactor 5 operates under the following conditions:
P=3 MPa
LHSV=6 h$^{-1}$
H$_2$/HC=100 Nm$^3$ per m$^3$ of feed The HR648 catalyst based on nickel and molybdenum sold by AXENS is used in the reactor 5.

The effluent originating from the reactor 5 is cooled to 45° C. and 2.5 MPa in the feed effluent heat exchanger 2 then in the air cooler 8, in order to then separate the gaseous phase enriched with hydrogen from the liquid phase in the flask 10.

Through the pipe 11, with complete recompression by the compressor 12, the gaseous phase is recycled to the feed 1 of the reactor 5, while the liquid effluent 15 which contains 190 ppb by weight metallic mercury is sent to the fractionation 20, passing through the heat exchangers 17 and 18.

The thirty-plate column 20 operates under 1.6 MPa with a bottom temperature of 195° C. and a reflux ratio of 0.25 by weight in relation to the feeding.

The 99.4 tonnes/h of liquid 21 recovered at the bottom of the column, which feeds the heat exchangers 17 and 18, contains less than 1 ppb by weight mercury and less than 0.5 ppm by weight sulphur and nitrogen and can be sent to reforming after fractionation without additional treatment in order to reduce the amount of mercury therein.

The vapour distillate 33 recovered at the head of the column which contains 21,800 micrograms of mercury per Nm$^3$ of gas is treated on a sulphur-containing alumina-type collection material distributed into two switchable adsorbers 43 to allow a continuous operation during the regeneration of the collection material. Each adsorber contains 2.5 tonnes of product from the Axtrap 200 series sold by Axens and operates at 40° C. A gaseous effluent is obtained which contains less than 0.1 micrograms of mercury per Nm$^3$ of gas, according to the needs of the refiners.

EXAMPLE 2

Not According to the Invention

Example 2, presented below, describes the operation of the process according to the prior art illustrated by U.S. Pat. No. 5,384,040.

100 tonnes/h of a feed consisting of a gas condensate contaminated by mercury is treated. This C5-300° C. condensate has a density of 0.737 kg/m$^3$ and contains 200 ppm by weight sulphur, 5 ppm by weight nitrogen and 190 ppb by weight mercury. In this example the ppm and ppb are expressed by weight.

The mercury speciation of this refinery gasoline has the following composition:

| Type of mercury | % | ppb wt |
|---|---|---|
| Hg° (mercury in metallic form) | 87% | 165 |
| HgS (mercury in particulate form) | 11% | 21 |
| Hg in ionic form | 1% | 2 |
| Hg in organometallic form | 1% | 2 |
| Total | 100% | 190 |

The first step is a step of converting mercury in organometallic form to metallic mercury in the presence of a catalyst and hydrogen at a pressure of 3 MPa and a temperature of 280° C.

The reactor operates under the following conditions:
P=3 MPa
LHSV=6 h$^{-1}$
H$_2$/HC=10 Nm$^3$ per m$^3$ of feed, or an H2/volume of catalyst ratio=60 vol/vol under normal conditions.

The HR648 catalyst based on nickel and molybdenum sold by AXENS is used in the reactor.

A gaseous phase comprising the excess hydrogen is separated from the liquid phase at the level of the reflux flask. The liquid effluent is fractionated into two cuts. The light fraction (85.4 tonnes/h) having a boiling temperature below 190° C. contains volatile mercury (more than 30 ppb) and is brought into contact with a collection material at a low temperature which makes it possible to reduce the amount of mercury therein to less than 5 ppb by mass.

On the other hand, the 14.4 tonnes/h of heavy fraction having a boiling temperature above 190° C. contains 146 ppb mercury and the described process therefore does not allow complete elimination of the mercury in the treated feed.

EXAMPLE 3

According to the Invention—Comparison with Example 2

This example is carried out according to the variant described with reference to FIG. 1 in which the separator 46, the collection materials 24 and 48 and the lines 47 and 49 are not used, but the mercury collection material 43 is used, and a collection material is also arranged on the line 50.

100 tonnes/h of the same gas condensate contaminated by mercury as in Example 2 is treated.

This feed is mixed with 583 kg/h hydrogen at 78% purity before being brought to a temperature of at least 280° C., then introduced into the reactor where the reactions of hydrogenolysis of all the mercury compounds into elemental mercury take place.

The reactor operates under the following conditions:
P=3 MPa
LHSV=6 h$^{-1}$
H$_2$/HC=10 Nm$^3$ of added hydrogen per m$^3$ of feed, or an H2/volume of catalyst ratio=60 vol/vol under normal conditions.

The HR648 catalyst based on nickel and molybdenum sold by AXENS is used in the reactor.

The effluent originating from the reactor 5 is cooled to 20° C. and 2.5 MPa in the feed effluent heat exchanger 2 then in the air cooler 8 before feeding the separator flask 10 which operates at 2.0 MPa. The gaseous fraction 11 produced is recycled to the reactor 5 at a throughput of 400 Nm3/m3 of feed, while the liquid fraction 15 feeds the fractionation column 20 in order to produce:

a gaseous distillate 33 comprising residual hydrogen and most of the metallic mercury two liquid cuts: a light cut 50 with a final boiling point at 190° C. and a heavy cut 21 with an initial boiling point at 190° C. and a final boiling point at 300° C.

After reflux (39), the gaseous distillate 42 recovered at the head of the column (0.6 t/hr), which contains 18,400 micrograms of mercury per Nm3 of gas, is treated on a sulphur-containing alumina-type collection material 43 distributed into two switchable adsorbers to allow a continuous operation during the regeneration of the collection material. Each adsorber contains 2.5 tonnes of product from the AxTrap 200 series sold by Axens and operates at 40° C. A gaseous effluent is obtained which contains less than 0.1 micrograms of mercury per Nm3 of gas, according to the needs of the refiners.

The 85 tonnes/h of liquid of the light cut 50 contains a very small proportion of the metallic mercury produced in the hydrogenolysis step and is conveyed at a low temperature over a collection material from the AxTrap 200 series sold by Axens in order to reduce the amount of mercury therein to below 5 ppb by weight.

The 14.4 tonnes/h of liquid of the heavy cut 21 recovered at the bottom of the column 20 contains less than 1 ppb mercury, which constitutes a clear progress compared with Example 2.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for elimination of mercury contained in a liquid hydrocarbon feed comprising mercury compounds, comprising:
   a) mixing the feed (1) with a hydrogen stream (14) and a gaseous fraction (11; 13) originating from step c),
   b) contacting the mixture obtained in step a) (5) with a catalyst at a temperature of 270° C. to 360° C. and at a pressure of 1.5 MPa to 7 MPa, in order to convert the mercury compounds to elemental mercury so as to produce an effluent containing elemental mercury,
   c) cooling said effluent containing elemental mercury (2; 8) to a temperature of 20° C. and 80° C., then, at a pressure of 1.5 MPa to 3.5 MPa and at a temperature of 20° C. to 80° C., separating (10) said effluent containing the elemental mercury into a gaseous fraction (11) and a liquid fraction (15), recycling, at least a part of said gaseous fraction (11; 13) to a),
   d) fractionating (20) of said liquid fraction at a pressure of 0.5 MPa to 2.0 MPa in order to produce a gaseous phase (42) and a liquid phase (21) comprising at least 95% by weight of the throughput of said liquid hydrocarbon feed,
   e) contacting at least a part of the gaseous phase (33; 42) produced in step d) with a mercury collection material (43).

2. The process according to claim 1, comprising drawing off and discharging a portion (45) of said gaseous fraction obtained in c) from the process and mixing said portion (45) of said gaseous fraction with the gaseous phase (33; 42) produced in d).

3. The process according to claim 1, in which the catalyst comprises at least one of nickel or cobalt, arranged on a support of alumina, silica-alumina, silica, zeolite, activated carbon, clay or aluminous cement.

4. The process according to claim 1, in which the collection material (43) comprises at least one of: copper oxide, lead oxide, copper sulfide, lead sulfide, sulfur on alumina, activated carbon, or doped molecular sieves.

5. The process according to claim 1, in which d) is carried out in a distillation column (20), the gaseous phase (33) being obtained directly at the head of the distillation column.

6. The process according to claim 1, in which d) is carried out in a distillation column (20), the gaseous stream produced at the head of the distillation column being partially condensed by cooling (34; 36) so as to produce said gaseous phase (42) and a condensate which is recycled to the head of the column as reflux.

7. The process according to claim 1, in which e) is carried out at a temperature below 150° C. and with a VVH of 1 to 50 h$^{-1}$.

8. The process according to claim 1, in which, before d), the water contained in the liquid fraction (15) is extracted (46).

9. The process according to claim 8, in which the extracted water (47) is brought into contact with a mercury collection material (48).

10. The process according to claim 1, in which the liquid phase (21; 23) obtained in d) is brought into contact with a mercury collection material (24).

11. The process according to claim 1, in which the liquid phase produced in d) is divided and separated into a first liquid part and a second liquid part, the first liquid part comprising lighter compounds than the compounds of the second liquid part, and in which the first liquid part is brought into contact with a mercury collection material.

12. The process according to claim 11, in which the first liquid part comprising the light compounds has a final distillation point below 100° C.

* * * * *